US010610561B2

(12) United States Patent
Qin et al.

(10) Patent No.: US 10,610,561 B2
(45) Date of Patent: Apr. 7, 2020

(54) CERAMIDE PRODUCTION-ACCELERATING AGENT

(71) Applicants: Zhongshan Hospital of Fudan University, Shanghai (CN); Kao Corporation, Tokyo (JP)

(72) Inventors: Wan Zhang Qin, Shanghai (CN); Chun Xin Yang, Shanghai (CN); Fan Qi Kong, Shanghai (CN); Hiroshi Nojiri, Tokyo (JP); Shotaro Ito, Tokyo (JP)

(73) Assignees: Zhongshan Hospital of Fudan University, Shanghai (CN); Kao Corporation, Tokyo (JP)

( * ) Notice: Subject to any disclaimer, the term of this patent is extended or adjusted under 35 U.S.C. 154(b) by 1314 days.

(21) Appl. No.: 14/600,701

(22) Filed: Jan. 20, 2015

(65) Prior Publication Data

US 2015/0132415 A1  May 14, 2015

Related U.S. Application Data

(62) Division of application No. 13/059,329, filed as application No. PCT/CN2009/073291 on Aug. 17, 2009, now abandoned.

(30) Foreign Application Priority Data

| Aug. 18, 2008 | (CN) | 2008 1 0145899 |
| Aug. 18, 2008 | (CN) | 2008 1 0145900 |
| Mar. 4, 2009 | (CN) | 2009 1 0118746 |
| Mar. 4, 2009 | (CN) | 2009 1 0118747 |

(51) Int. Cl.

| A61K 36/898 | (2006.01) |
| A61Q 19/00 | (2006.01) |
| A61K 8/97 | (2017.01) |
| A61K 36/232 | (2006.01) |
| A61K 36/284 | (2006.01) |
| A61K 36/346 | (2006.01) |
| A61K 36/484 | (2006.01) |
| A61K 36/533 | (2006.01) |
| A61K 36/64 | (2006.01) |
| A61K 36/70 | (2006.01) |
| A61K 36/708 | (2006.01) |
| A61K 36/8945 | (2006.01) |

(52) U.S. Cl.
CPC .......... A61K 36/898 (2013.01); A61K 8/97 (2013.01); A61K 36/232 (2013.01); A61K 36/284 (2013.01); A61K 36/346 (2013.01); A61K 36/484 (2013.01); A61K 36/533 (2013.01); A61K 36/64 (2013.01); A61K 36/70 (2013.01); A61K 36/708 (2013.01); A61K 36/8945 (2013.01); A61Q 19/00 (2013.01)

(58) Field of Classification Search
None
See application file for complete search history.

(56) References Cited

U.S. PATENT DOCUMENTS

| 2004/0005370 | A1* | 1/2004 | Breton | A61K 8/31 424/757 |
| 2008/0260655 | A1* | 10/2008 | Tamarkin | A61K 8/046 424/45 |
| 2011/0200694 | A1 | 8/2011 | Qin et al. | |

FOREIGN PATENT DOCUMENTS

| CN | 1203097 A | 12/1998 |
| CN | 1248436 A | 3/2000 |
| CN | 1395937 A | 2/2003 |
| CN | 1437930 A | 8/2003 |
| CN | 1533701 A | 10/2004 |
| CN | 1947696 A | 4/2007 |
| CN | 1977809 A * | 6/2007 |
| CN | 1977812 A | 6/2007 |
| CN | 101011333 A | 8/2007 |
| CN | 101062002 A | 10/2007 |
| EP | 0 993 822 A1 | 4/2000 |
| JP | 1985-258104 A | 12/1985 |
| JP | 05-097653 A | 4/1993 |
| JP | 05-155751 A | 6/1993 |
| JP | 09-176030 A | 7/1997 |
| JP | 10-139639 A | 5/1998 |
| JP | 10-152421 A | 6/1998 |
| JP | 11-180856 A | 7/1999 |
| JP | 2000-053533 A | 2/2000 |

(Continued)

OTHER PUBLICATIONS

Chan et al., Antioxidant Activity of Chinese Medicinal Herbs, 2008, Pharmaceutical Biology, 46: 587-595.*

(Continued)

Primary Examiner — Terry A McKelvey
Assistant Examiner — Catheryne Chen
(74) Attorney, Agent, or Firm — Sterne, Kessler, Goldstein & Fox P.L.L.C.

(57) ABSTRACT

The present invention provides a pharmaceutical composition or a cosmetic product which can accelerate production of ceramide in cells. The ceramide production-accelerating agent contains a plant selected from the group consisting of Radix Heraclei Scabridi, Rhizoma Dioscoreae, Radix Rehmanniae, Rhizoma Atractylodis Macrocephalae, Radix Glycyrrhizae, Radix Et Rhizoma Rhei, Pseudobulbus Bletillae, Radix Polygoni Multiflori, Radix Platycodi, and Herba Leonuri, or an extract thereof as an active ingredient. Further, the present invention provides a moisturizing agent containing a plant selected from the group consisting of Herba Leonuri and Rhizoma Dioscoreae, or an extract thereof as an active ingredient.

9 Claims, No Drawings

(56) References Cited

FOREIGN PATENT DOCUMENTS

| JP | 2000-169359 A | 6/2000 |
|---|---|---|
| JP | 2000-281528 A | 10/2000 |
| JP | 2000-281553 A | 10/2000 |
| JP | 2001-158735 A | 6/2001 |
| JP | 2001-158736 A | 6/2001 |
| JP | 2003-277223 A | 10/2003 |
| JP | 2006-124350 A | 5/2006 |
| JP | 2006-342066 A | 12/2006 |
| JP | 2006-347902 A | 12/2006 |
| JP | 2006-347907 A | 12/2006 |
| JP | 2008-255051 A | 10/2008 |

OTHER PUBLICATIONS

International Search Report (ISR) for PCT/CN2009/073291, I.A. fd: Aug. 17, 2009, dated Dec. 3, 2009 from the State Intellectual Property Office, the P.R. China, Beijing, China.
International Preliminary Report on Patentability (IPRP), Chapter I of the Patent Cooperation Treaty, including the Written Opinion PCT/CN2009/073291, I.A. fd: Aug. 17, 2009, dated Feb. 22, 2011 from the International Bureau of WIPO, Geneva, Switzerland.
Modrak, De et al., "Sphingolipid targets in cancer therapy," Mol. Cancer Ther. 5: 200-208 (Feb. 2006), American Association for Cancer Research, Inc., Philadelphia, PA.
"Angelica Dahurica Root," Tennen iyaku shigengaku (Natural Medicinal Resources), 2$^{nd}$ Edition, Tadahiro Takeda et al., eds., Hirokawa-shoten, Japan, publisher, pp. 215-216 (1997).
"Rehmanniae radix/Rehmannia Root," Tennen iyaku shigengaku (Natural Medicinal Resources), 2$^{nd}$ Edition, Tadahiro Takeda et al., eds., Hirokawa-shoten, Japan, publisher, pp. 132-133 (1997).
"Glycyrrhizae Radix," Waken yakubutsugaku (Japanese, Chinese Medicines), 1$^{st}$ Edition, Keijiro Takagi et al., eds., Nanzando, Japan, publisher, pp. 72-73 (1982).
"D5 (Orchidaceae): Monocotyledon rope/Orchidaceae," Waken Yakuyo shokubutsu (Japanese and Chinese Medicinal Plants), 20$^{th}$ Edition, Tatsuo Karibe, ed., Hirokawa-shoten, Japan, publisher, p. 359 (1977).
"Leonurus sibiricus/Leonurus sibiricus Linne," Waken Yakuyo shokubutsu (Japanese and Chinese Medicinal Plants), 20$^{th}$ Edition, Tatsuo Karibe, ed., Hirokawa-shoten, Japan, publisher, p. 72 (1977).
"Dioscorea Rhizone/Dioscoreae Rhizoma," Tennen iyaku shigengaku (Natural Medicinal Resources), 2$^{nd}$ Edition, Tadahiro Takeda et al., eds., Hirokawa-shoten, Japan, publisher, pp. 263-264 (1997).
Du, Xing-xu et al., "Progress of study on coumarin of angelicae dahuricae," Journal of Jinggangshan Medical College 26(2): 120-122 (2005), Jinggangshan Medical College, China.
Zhang, Xiuli et al., "Study on the Separation and Purification Technology of Catalpol from Rehmannia by Macroporous Adsorption Resins," China Biotechnology 28(1): 65-69 (Jan. 2008), China Academic Journal Electronic Publishing House, China.
Hu, Rong et al., "The Effect of Various Solutions Extracted from Atractylodes Rhizoma and Poria on the Activity of Tyrosinase," Journal of Sichuan of Traditional Chinese Medicine 26(5): 27-28 (May 2008), China Academic Journal Electronic Publishing House, China.
Ji, Chenfeng et al.,, "Study on Chemistry and Pharmacology of Glycyrrhiza Polysaccharide," Journal of Harbin University of Commerce (Natural Sciences Edition) 20(5): 515-518 (Oct. 2004), China Academic Journal Electronic Publishing House, China.

Ding, Changshan et al., "The Cosmetic Containing Rheum," Flavour Fragrance Cosmetics, No. 4, pp. 14-15 (1993), China Academic Journal Electronic Publishing House, China.
Lu, Bo et al., "Effect of Different Extracts from Bletilla Colloid on Rabbit Platelet Aggregation," Pharmaceutical Journal of Chinese People's Liberation Army 21(5): 330-332 (2005), China Academic Journal Electronic Publishing House, China.
Xia, Zadan et al., "Measuring the contents of total flavonoids in the Uyghur Traditional Medical Plant—*Polygonum mulflorum* by Spectrophotometer," Food Science 27(12): 704-705 (2006), China Academic Journal Electronic Publishing House, China.
Fu, Wenwei et al., "Review on Chemical components and bioactivities of Platycodon grandiflorum," Journal of Shenyang Pharmaceutical University 23(3): 184-191 (Mar. 2006), China Academic Journal Electronic Publishing House, China.
Liu, Hongyan et al., "Toxicity of Petroleum Ether Extract from Herba Leonuri on Rat Renal Tubular Epithelial Cells," Acta Academiae Medicinae CPAF 17(12): 1096-1101 (Jul. 2008), China Academic Journal Electronic Publishing House, China.
Wang, Yong et al., "Analysis of Fatty Acids from Dioscorea opposita Thumb.," Journal of Xinxiang Medical College 25(2): 112-113 (Mar. 2008), China Academic Journal Electronic Publishing House, China.
Wei, Jing et al.,, "Function of Ceramides in Skin and Application in Cosmetic," Cereals & Oils No. 1, 21-24 (2007) China Academic Journal Electronic Publishing House, China.
Notification of First Office Action for CN Application No. 200910118746.1, dated Jan. 13, 2012, Patent Office of the People's Republic of China, Beijing, China.
Notification of Second Office Action for CN Application No. 200910118746.1, dated Aug. 7, 2012, Patent Office of the People's Republic of China, Beijing, China.
Notification of First Office Action for CN Application No. 200910118747.6, dated Jan. 21, 2012, Patent Office of the People's Republic of China, Beijing, China.
Notification of Second Office Action for CN Application No. 200910118747.6, dated Aug. 7, 2012, Patent Office of the People's Republic of China, Beijing, China.
Notification of Third Office Action for CN Application No. 200910118746.1, dated Jan. 5, 2013, Patent Office of the People's Republic of China, Beijing, China.
Notification of Third Office Action for CN Application No. 200910118747.6, dated Dec. 31, 2012, Patent Office of the People's Republic of China, Beijing, China.
Gu, Yueli and Gu, Jianghong, "The Progress of Research on Pharmacological Effects of Motherwort," Chinese J Traditional Medical Science and Technology, Jul. 2008, 15(4):320-321, Tsinghua Tongfang Knowledge Network Technology Co., Ltd., Beijing, China.
Extended European search report for EP Application No. 09807864.5, including the supplementary European search report and the European search opinion, dated Apr. 17, 2013, European Patent Office, Munich, Germany.
Nikko Chemicals Ltd et al., "Skin Roughness Inhibitor," in New Cosmetics Handbook, H. Tamura et al., eds., pp. 503-517 and 729-231, Oct. 30, 1996, Chuo Printing Co., Ltd., Osaka, Japan.
Luo, et al., "Toxicity of Petroleum Ether Extract from Herba Leonuri after Oral administration in Rats," Clinical Pharm, Apr. 2008, 43:499-501.
Excepted file history, U.S. Appl. No. 13/059,329, 35 U.S.C. § 371 date: Mar. 22, 2011, United States Patent and Trademark Office, Alexandria, VA.

\* cited by examiner

CERAMIDE PRODUCTION-ACCELERATING AGENT

FIELD OF THE INVENTION

The present invention relates to a ceramide production-accelerating agent which can increase ceramide.

BACKGROUND OF THE INVENTION

Ceramide, which is a sphingolipid, is a lipid contained only in a small amount in whole living body. It has recently been reported that phenomena, such as proliferation, differentiation, and growth inhibition are induced by enhancing production of intracellular ceramide, and thus ceramide is an attractive intracellular signaling molecule capable of controlling proliferation, differentiation, apoptosis, and the like, of cells. Accordingly, it is thought that a ceramide production-accelerating substance is expected to have effects such as suppression of proliferation, induction of differentiation, and induction of apoptosis of animal cells, and consequently is expected to have therapeutic effects on diseases caused by abnormality of proliferation or differentiation of cells, such as inflammatory diseases and malignant tumors (Non-Patent Document 1).

In addition, ceramide, which is a sphingolipid, makes up at least half of lipids contained in horny layer, which is outermost layer of skin, and plays an important role in moisturizing function and barrier function of skin. Ceramide is produced in and secreted from keratinocytes and then functions as forming a lamella structure in intracellular space of the horny layer.

However, there are many reports showing that normal metabolism of ceramide is prevented and thus the amount of ceramide in horny layer is decreased to cause impairment of moisturizing function, barrier function, and the like, of the skin in dermal diseases such as dry skin, xerosis, atopic dermatitis, senile xerosis and psoriasis.

Therefore, a method of supplying the decreased ceramides topically to treat such diseases has been attempted. However, problems included in this method are, for example, difficulty of long-term effect and low stability, and the like.

Meanwhile, it is reported that ceramide shows bone resorption inhibitory action, bone reinforcing action, and alveolar bone loss inhibitory action, is useful for prevention and amelioration of bone and joint diseases, such as osteoporosis, bone fracture, lumbago, and rheumatism (Patent Document 1), and further that it is effective for prevention of periodontal disease (Patent Document 2). Accordingly, a ceramide production-accelerating substance is also expected to show therapeutic effect on such diseases.

Moreover, ceramide is reported to show action of giving body and elasticity to hair and improving feeling thereof (Patent Document 3), and thus a ceramide production-accelerating substance is also expected to show such effects.

*Angelicae Dahuricae Radix, Rehmanniae Radix, Atractylodis Rhizoma, Glycyrrhizae Radix, Rhei Rhizoma, Bletilla Tuber, Polygoni Multiflori Radix, Platycodi Radix, Leonuri Herba*, and *Dioscoreae Rhizoma* are all medicinal plants which have been used since a long time ago as a folk medicine or herbal medicine. Specifically, *Angelicae Dahuricae Radix* is used for the purpose of alleviation of fever, pain relief, detoxication, pus discharge, and the like as a harval medicine, and its ether extract is reported to show blood pressure elevation action and respiratory movement excitation action (Non-Patent Document 2). *Rehmanniae Radix* is applied, as a tonic medicine or antipyretic drug, to diabetes, prostatomegaly, senile lumbago, cataract, and the like, and is used as a Chinese medicine for the purpose of blood replenishment, tonic, alleviation of fever, antidiarrheal, laxativeness, and the like. Also, a water extract or ethanol extract of *Rehmanniae Radix* is reported to show hypoglycemic or hyperglycemic inhibitory action, laxativeness, and diuretic action (Non-Patent Document 3). *Atractylodis Rhizoma* is used for the purpose of stomach strengthening, intestinal function regulation, diuresis, suppression of sweating, and the like, and is reported to show urinary volume increasing action and hyperglycemic action. *Glycyrrhizae Radix* is known as a source for glycyrrhizinic acid and it is widely used as an antitussive or expectorant drug, or a remedy for gastrointestinal ulcer, and is used as a Chinese medicine for the purpose of pain relief, detoxication, and the like. An extract of *Glycyrrhizae Radix* is reported to show remarkable gastric inhibitory action, gastrointestinal ulcer recovery accelerating action, antispasmodic action, antitussive action, and the like (Non-Patent Document 4). *Rhei Rhizoma* is used as a purgative and a stomachic, and is used as a Chinese medicine for the purpose of anti-inflammation, purgation, and detoxication. *Bletilla Tuber* is used as a Chinese medicine for the purpose of hemostasis, pain relief, and chronic gastritis (Non-Patent Document 5). *Polygoni Multiflori Radix* is used as a Chinese medicine for dizziness or headache due to anemia, and insomnia. *Platycodi Radix* is used as an antitussive and expectorant drug, and is known to have saliva secretion and respiratory secretion accelerating action. *Leonuri Herba* is used against various symptoms of women before and after childbirth as a medicine for blood activation, increased metabolism, and energy supplement, and is reported to be effective against edema due to nephritis (Non-Patent Document 6). *Dioscoreae Rhizoma* is used for the purpose of nutritional fortification, antitussive, antidiarrheal, and dryness relief, and is reported to show antihypertensive action and androgenic hormone enhancing action (Non-Patent Document 7).

However, it has not so far been known that these plants show a ceramide production-accelerating effect and a moisturizing effect.

[Patent Document 1] JP-A-2001-158736
[Patent Document 2] JP-A-2001-158735
[Patent Document 3] JP-A-H10-152421
[Non-Patent Document 1] Sphingolipid targets in cancer therapy, David E. Modrak et al., Molecular Cancer Therapeutics, 2006, 5(2): 200-8
[Non-Patent Document 2] Tennen iyaku shigengaku (Natural Medicinal Resources) (2nd Edition, edited by Tadahiro TAKEDA et al., and published by Hirokawa-shoten), pp. 215-216
[Non-Patent Document 3] Tennen iyaku shigengaku (Natural Medicinal Resources) (2nd Edition, edited by Tadahiro TAKEDA et al., and published by Hirokawa-shoten), pp. 132-133
[Non-Patent Document 4] Wakan yakubutsugaku (Japanese, Chinese Medicines) (1st Edition, edited by Keijiro TAKAGI et al., and published by Nanzando), pp. 72-73.
[Non-Patent Document 5] Tennen iyaku shigengaku (Natural Medicinal Resources) (2nd Edition, edited by Tadahiro TAKEDA et al., and published by Hirokawa-shoten), pp. 263-264
[Non-Patent Document 6] Wakan Yakuyo shokubutsu (Japanese and Chinese Medicinal Plants) (20th Edition, edited by Tatsuo KARIBE, and published by Hirokawa-shoten), p. 72

[Non-Patent Document 7] Tennen iyaku shigengaku (Natural Medicinal Resources) (2nd Edition, edited by Tadahiro TAKEDA et al., and published by Hirokawa-shoten), pp. 263-264

SUMMARY OF THE INVENTION

The present invention provides pharmaceuticals, cosmetics, and the like for accelerating intracellular ceramide production. In addition, the present invention provides cosmetics or pharmaceuticals capable of restoring or maintaining barrier function and moisturizing function of skin.

The present inventors have searched for highly safe natural materials, and have found that an extract of each of *Angelicae Dahuricae Radix, Rehmanniae Radix, Atractylodis Rhizoma, Glycyrrhizae Radix, Rhei Rhizoma, Bletilla Tuber, Polygoni Multiflori Radix, Platycodi Radix, Leonuri Herba,* and *Dioscoreae Rhizoma* shows ceramide production-accelerating action and can be used as a ceramide production accelerating-agent.

The present invention relates to a ceramide production-accelerating agent containing a plant selected from *Angelicae Dahuricae Radix, Rehmanniae Radix, Atractylodis Rhizoma, Glycyrrhizae Radix, Rhei Rhizoma, Bletilla Tuber, Polygoni Multiflori Radix, Platycodi Radix, Leonuri Herba,* and *Dioscoreae Rhizoma*, or an extract thereof as an active ingredient.

The extract of *Angelicae Dahuricae Radix, Atractylodis Rhizoma, Bletilla Tuber, Polygoni Multiflori Radix, Platycodi Radix, Leonuri Herba,* or *Dioscoreae Rhizoma* may be a petroleum ether extract prepared by using a petroleum ether as an extraction solvent. The extract of *Rehmanniae Radix* or *Glycyrrhizae Radix* may be an ethanol extract prepared by successively using a petroleum ether and ethanol as extraction solvents. The extract of *Rhei Rhizoma* may be a water extract prepared by successively using a petroleum ether, ethanol, and water as extraction solvents.

Also, the present invention relates to use of a plant selected from *Angelicae Dahuricae Radix, Rehmanniae Radix, Atractylodis Rhizoma, Glycyrrhizae Radix, Rhei Rhizoma, Bletilla Tuber, Polygoni Multiflori Radix, Platycodi Radix, Leonuri Herba,* and *Dioscoreae Rhizoma* or an extract thereof for the manufacture of a ceramide production-accelerating agent.

Moreover, the present invention relates to a moisturizing agent containing a plant selected from *Leonuri Herba* and *Dioscoreae Rhizoma* or an extract thereof as an active ingredient.

The extract of the *Leonuri Herba* or *Dioscoreae Rhizoma* in the moisturizing agent may be a petroleum ether extract prepared by using a petroleum ether as an extraction solvent.

Also, the present invention relates to use of a plant selected from *Leonuri Herba* and *Dioscoreae Rhizoma* or an extract thereof for the manufacture of a moisturizing agent.

The ceramide production-accelerating agent of the present invention increases intracellular ceramide and is useful as pharmaceuticals, and the like, for preventing or ameliorating inflammatory disease, bone and joint disease, periodontal disease, and the like, or as cosmetics, and the like, for giving body and strength to hair and improving the feeling thereof.

The present inventors have searched for highly safe natural materials, and found that certain plants or extract thereof has ceramide production-accelerating action and they are useful as pharmaceuticals or cosmetics which can restore or maintain barrier function and moisturizing function of horny layer.

The ceramide production-accelerating agent of the present invention is useful as cosmetics, pharmaceuticals, and the like, for restoring or maintaining barrier function and moisturizing function of skin by increasing ceramide in horny layer.

DETAILED DESCRIPTION OF THE INVENTION

In the present invention, *Angelicae Dahuricae Radix* is originated from *Angelica dahurica* Bentham et Hooker belonging to Umbelliferae; *Rehmanniae Radix* is originated from *Rehmannia glutinosa* Liboschitz var. *purpurea* Makino or *Rehmannia glutinosa* Liboschitz belonging to Scrophulariaceae; *Atractylodis Rhizoma* is originated from *Atractylodes ovata* De Candolle belonging to Compositae; *Glycyrrhizae Radix* is originated from *Glycyrrhiza uralensis* Fisher or *G. glabra* Linne belonging to Leguminosae; *Rhei Rhizoma* is originated from *Rheum palmatum* L. belonging to Polygonaceae; *Bletilla Tuber* is originated from *Bletilla striata* Reichb. fil. belonging to Orchidaceae; *Polygoni Multiflori Radix* is originated from *Polygonum multiflorum* Thunb. belonging to Polygonaceae; *Platycodi Radix* is originated from *Platycodon grandiflorum* A. De Candolle belonging to Campanulaceae; *Leonuri Herba* is originated from *Leonurus sibiricus* L. belonging to Laminaceae; and *Dioscoreae Rhizoma* is originated from *Dioscorea japonica* Thunberg belonging to Dioscoreaceae.

Whole plant body, leaves, barks, branches, fruits, or roots of the above plants may be used directly or after pulverization, preferably roots of *Angelicae Dahuricae Radix* and *Rehmanniae Radix*; roots, and stems of *Atractylodis Rhizoma*; roots and rhizomes of *Glycyrrhizae Radix* and *Rhei Rhizoma*; tubers of *Bletilla Tuber*; roots of *Polygoni Multiflori Radix*; roots of *Platycodi Radix*; aboveground parts of *Leonuri Herba*; and roots and stems of *Dioscoreae Rhizoma* are used.

The plant extracts of the present invention include extracts prepared by providing the parts to be used of the above-mentioned plants directly or after drying and cutting into a suitable size or pulverization before extraction therefrom, and also include fractions (ingredients) showing higher activity prepared by further isolation and purification thereof.

The extraction may be performed by immersion into a solvent at room temperature or under heating or by solvent extraction conducted by using an extraction equipment such as Soxhlet extractor, and further by extraction through distillation such as steam distillation, supercritical fluid extraction using supercritical carbon dioxide, or compression method to obtain extract by compression.

Either polar solvent or non-polar solvent, or a mixture thereof, may be used as solvent for extraction used in the solvent extraction. Examples thereof include water; alcohols such as methanol, ethanol, propanol, and butanol; polyols such as ethylene glycol, propylene glycol, and butylene glycol; ketones such as acetone and methylethylketone; esters such as methyl acetate and ethyl acetate; linear or cyclic ethers such as tetrahydrofuran and diethylether; polyethers such as polyethylene glycol; halogenated hydrocarbons such as dichloromethane, chloroform and carbon tetrachloride; hydrocarbons such as hexane, cyclohexane and petroleum ether; aromatic hydrocarbons such as benzene and toluene; pyridines; supercritical carbon dioxide; fats and oils, waxes, and other oils, which may be used alone or in combinations of two or more, and the extraction may be performed repeatedly with changing of solvents. Among these solvents, it is preferable to use water, ethanol, propylene glycol, butylene glycol, petroleum ether, and the like; more preferably, a mixture of water and ethanol, or petroleum ether.

In the case where, for example, water, alcohol, hydrocarbon or a mixture of water and an alcohol is used for extraction, the extraction is preferably performed by extraction using 1 to 50 parts by mass of the solvent relative to 1 part by mass of the plant at a temperature of 4 to 100° C., more preferably 20 to 80° C., for 1 hour to 30 days, more preferably 1 hour to 10 days.

Examples of the methods of isolating and purifying the extract include an activated charcoal treatment, liquid-liquid distribution, column chromatography, liquid chromatography, gel filtration, and precision distillation. If needed, an additional treatment, such as deodorization and decolorization, may be performed following a known method.

Thus prepared plant extract of the present invention may be used as a liquid extraction or a fraction directly, or may be used as a diluted liquid prepared by dilution thereof with an appropriate solvent, an extract, a dried powder, or a paste prepared through concentration under heat or under reduce pressure may be used. The plant extract may be freeze-dried, and upon using may be diluted with a solvent which is commonly used for extraction, such as water, ethanol, propylene glycol, butylene glycol, a water-ethanol mixture, a water-propylene glycol mixture, and a water-butylene glycol mixture. It may also be used in the form of being contained in a vesicle, such as liposome, or a microcapsule, and the like.

The plants or the extracts thereof of the present invention show the action of increasing an amount of ceramide in a normal human keratinocyte, as shown in below Examples.

Ceramide plays an important role in moisturizing function and barrier function of the skin (Genji IMOKAWA, Koshokaishi 1(4), 250-253, 1991). The moisturizing function herein means a function which gives the skin appropriate moisture to make the skin soft and make the skin smooth and beautiful. The barrier function herein means a function which prevents evaporation of the moisture in the body to prevent the body from drying out and prevent invasion of foreign substance from outside into the body.

Accordingly, the plants or the extracts thereof of the present invention can be used as a ceramide production-accelerating agent, a moisturizing agent, or a barrier reinforcing agent, and can be used for manufacturing the ceramide production-accelerating agent, moisturizing agent, or barrier reinforcing agent. The ceramide production-accelerating agent or moisturizing agent can be used as pharmaceuticals, quasi drugs, and cosmetics for increasing ceramide in horny layer and restoring or maintaining barrier function and moisturizing function of the skin. The ceramide production-accelerating agent is expected to exhibit effects such as suppression of proliferation of animal cells, induction of differentiation, and induction of apoptosis, therefore, it can be used as pharmaceuticals or quasi drugs for preventing or treating diseases caused by abnormal proliferation or differentiation of cells, such as inflammatory diseases and malignant tumors (the above-described Non-Patent Document 1), and also can be used as pharmaceuticals or quasi drugs for prevention and amelioration of bone and joint diseases, such as osteoporosis, fracture of bone, lumbago, and rheumatism, and as pharmaceuticals or quasi drugs for prevention and amelioration of periodontal disease (the above-described Patent Documents 1 and 2). Moreover, it can be used as quasi drugs or cosmetics for giving body and elasticity to the hair, and improving the feeling thereof (the above-described Patent Document 3). The ceramide production-accelerating agent can be used as quasi drugs or cosmetics which are based on the concept of ceramide production-acceleration and moisturizing, and if needed, on which such a concept is indicated.

The dosage form in the case where the ceramide production-accelerating agent or moisturizing agent of the present invention is used as pharmaceuticals may be either oral administration with tablets, capsules, granules, powders, syrups, and the like, or parenteral administration with injections, external preparations, suppositories, transdermal drugs, and the like. When preparing the pharmaceutical preparation, the plants or the extracts thereof of the present invention may be used alone, or in appropriate combination with a pharmacologically acceptable excipient, binder, extender, disintegrant, surfactant, lubricant, dispersing agent, buffering agent, preservative, corrigent, fragrance, film forming agent, carrier, diluent, and the like. The content of the plants of the present invention in the preparation is preferably 0.01 to 20% by mass, more preferably, 0.05 to 10% by mass in terms of dry solid content, and the content of the plant extract is preferably 0.0001 to 10% by mass, more preferably, 0.001 to 5% by mass in terms of solid content. When the ceramide production-accelerating agent of the present invention is used as pharmaceuticals, a daily dose per one adult, as the plants or the extracts thereof (in terms of dry solid content) is preferably 0.001 to 1000 mg, more preferably, 0.01 to 100 mg.

Moreover, when the ceramide production-accelerating agent and moisturizing agent of the present invention are used as quasi drugs or cosmetics, they may be formed as an external preparation for the skin, a detergent, or make-up cosmetics, and may be provided as various dosage forms, including lotions, milky lotions (emulsions), gels, creams, ointments, powders, and granules, in accordance with intended use. These quasi drugs and cosmetics with various dosage forms may be prepared by using the plants or the extracts of the present invention alone, or in appropriate combination with an oily ingredient, a moisturizing agent, a powder, a pigment, an emulsifying agent, a solubilizing agent, a detergent, an ultraviolet absorber, a thickening agent, a medicinal ingredient, a fragrance, a resin, an anti-microbial-antifungal agent, a plant extract, an alcohol, and the like. Examples of the medicinal ingredient include other moisturizing ingredients such as sodium hyaluronate.

The content of the plant of the present invention in the quasi drug or cosmetics is preferably 0.01 to 100% by mass, more preferably, 0.05 to 70% by mass, as a dry solid ingredient. Meanwhile, the content of the extract thereof is generally preferably 0.00001 to 100% by mass, more preferably, 0.0001 to 70% by mass, in terms of solid content.

The above-mentioned "quasi drug" is a cosmetic showing special effects defined in Article 2(2) of the Pharmaceutical Affairs Law of Japan, the effect is milder than that of pharmaceuticals.

EXAMPLES

Preparation Example 1

Preparation of *Angelicae Dahuricae Radix* Extract

To 100 g of *Angelicae Dahuricae Radix*, 5 times amount of petroleum ether was added, and the mixture was stirred for 1 hour at 50° C., followed by extraction and filtration, to prepare a petroleum ether extract. Then the petroleum ether extract was evaporated and dried, to yield approximately 0.9 g of petroleum ether extract of *Angelicae Dahuricae Radix*.

Preparation Example 2

Preparation of *Rehmanniae Radix* Extract

Following the same procedure as Preparation Example 1, except that 100 g of *Rehmanniae Radix* was used in place of 100 g of *Angelicae Dahuricae Radix*, a petroleum ether extract was prepared. To the residue prepared by the extraction with the petroleum ether, 5 times amount of 95% ethanol was added, and the mixture was refluxed with stirring at 78° C. for 1 hour, followed by extraction and filtration, to prepare an ethanol extract. Then the ethanol extract was evaporated and dried, to yield approximately 5.0 g of ethanol extract of *Rehmanniae Radix*.

Preparation Example 3

Preparation of *Atractylodis Rhizoma* Extract

Following the same procedure as Preparation Example 1, except that 100 g of *Atractylodis Rhizoma* was used in place of 100 g of *Angelicae Dahuricae Radix*, a petroleum ether extract was prepared. The petroleum ether extract was evaporated and dried, to yield approximately 0.8 g of petroleum ether extract of *Atractylodis Rhizoma*.

Preparation Example 4

Preparation of *Glycyrrhizae Radix* Extract

Following the same procedure as Preparation Example 1, except that 100 g of *Glycyrrhizae Radix* was used in place of 100 g of *Angelicae Dahuricae Radix*, a petroleum ether extract was prepared. To the residue prepared by the extraction with the petroleum ether, 5 times amount of 95% ethanol was added, and the mixture was refluxed at 78° C., and stirred for 1 hour, followed by extraction and filtration, to prepare an ethanol extract. Then the ethanol extract was evaporated and dried, to yield approximately 9.1 g of ethanol extract of *Glycyrrhizae Radix*.

Preparation Example 5

Preparation of *Rhei Rhizoma* Extract

Following the same procedure as Preparation Example 1, except that 100 g of *Rhei Rhizoma* was used in place of 100 g of *Angelicae Dahuricae Radix*, a petroleum ether extract was prepared. To the residue prepared by the extraction with the petroleum ether, 5 times amount of 95% ethanol was added, and the mixture was refluxed with stirring at 78° C. for 1 hour, followed by extraction and filtration, to prepare an ethanol extract. To the resulting residue prepared by the extraction with ethanol, 5 times amount of water was added and the mixture was stirred at 60° C. for 1 hour under ultrasonication, followed by extraction and filtration, to thereby prepare a water extract. Then this water extract was evaporated and dried, to yield approximately 6.9 g of water extract of *Rhei Rhizoma*.

Preparation Example 6

Preparation of *Bletilla Tuber* Extract

Following the same procedure as Preparation Example 1, except that 100 g of *Bletilla Tuber* was used in place of 100 g of *Angelicae Dahuricae Radix*, a petroleum ether extract was prepared. The petroleum ether extract was evaporated and dried, to yield 0.4 g of petroleum ether extract of *Bletilla Tuber*.

Preparation Example 7

Preparation of *Polygoni Multiflori Radix* Extract

Following the same procedure as Preparation Example 1, except that 100 g of *Polygoni Multiflori Radix* was used in place of 100 g of *Angelicae Dahuricae Radix*, a petroleum ether extract was prepared. The petroleum ether extract was evaporated and dried, to yield approximately 0.2 g of petroleum ether extract of *Polygoni Multiflori Radix*.

Preparation Example 8

Preparation of *Platycodi Radix* Extract

Following the same procedure as Preparation Example 1, except that 100 g of *Platycodi Radix* was used in place of 100 g of *Angelicae Dahuricae Radix*, a petroleum ether extract was prepared. The petroleum ether extract was evaporated and dried, to yield approximately 0.5 g of petroleum ether extract of *Platycodi Radix*.

Preparation Example 9

Preparation of *Leonuri Herba* Extract

Following the same procedure as Preparation Example 1, except that 100 g of *Leonuri Herba* was used in place of 100 g of *Angelicae Dahuricae Radix*, a petroleum ether extract was prepared. The petroleum ether extract was evaporated and dried, to yield approximately 0.5 g of petroleum ether extract of *Leonuri Herba*.

Preparation Example 10

Preparation of *Dioscoreae Rhizoma* Extract

Following the same procedure as Preparation Example 1, except that 100 g of *Dioscoreae Rhizoma* was used in place of 100 g of *Angelicae Dahuricae Radix*, a petroleum ether extract was prepared. The petroleum ether extract was evaporated and dried, to yield approximately 0.3 g of the petroleum ether extract of *Dioscoreae Rhizoma*.

Example 1

Ceramide Production Acceleration Test

<Test Solutions and Control Solutions>

| Preparation Example | Test solution | Control solution |
|---|---|---|
| 1, 3, 6, 7, 8, 9, and 10 (Petroleum ether extract) | Using ethanol as a solvent, 1% w/v content of each ethanol solution of the petroleum ether extract was prepared. | Ethanol |
| 2 and 4 (Ethanol extract) | Using ethanol as a solvent, 1% w/v content of each ethanol solution of the ethanol extract was prepared. | Ethanol |

-continued

| Preparation Example | Test solution | Control solution |
|---|---|---|
| 5 (Water extract) | Using 10% ethanol as a solvent, 1% w/v content of an ethanol solution of the water extract was prepared. | 10% ethanol |

<Culture Condition>

Normal human epidermal keratinocyte (NHEK (F)) was seeded into 6 well plate EpiLife-KG2 (product of KURABO Industries Ltd.), and was cultured until confluent. Then, the culture medium were changed to EpiLife-KG2 (without additive growth factor), and each of the above test solutions and each control solution were added thereto. After culturing for 3 days, cells were collected from the wells one by one.

<Lipid Extraction>

Lipid was extracted from the collected cells following Bligh and Dyer method. After the extraction, lipid extract was dried to solid with nitrogen, the solid was dissolved again in a mixed liquid of chloroform and methanol, to prepare a lipid sample. The amount of protein was quantified by BCA method.

<Analysis of Ceramide Level>

The extracted lipid was analyzed with a thin-layer chromatography (TLC). The lipid was horizontally developed twice with a solvent (chloroform:methanol:acetic acid 190:9:1), blow-dried, sprayed with a coloring solution of copper sulfate, and heated on a hot plate, whereby the ceramide was detected. Thereafter, the obtained values were divided by each protein amount to calculate each ceramide amount (Table 1). The values in the Table are relative values to the ceramide amount of control (a sample added the above-mentioned control solution) set as 1.

TABLE 1

| Plant extract | Ceramide amount (Relative value) |
|---|---|
| Angelicae Dahuricae Radix (petroleum ether extract) | 4.3 |
| Rehmanniae Radix (Ethanol extract) | 3.3 |
| Atractylodis Rhizoma (Petroleum ether extract) | 2.0 |
| Glycyrrhizae Radix (Ethanol extract) | 7.9 |
| Rhei Rhizoma (Water extract) | 4.7 |
| Bletilla Tuber (Petroleum ether extract) | 2.0 |
| Polygoni Multiflori Radix (Petroleum ether extract) | 5.1 |
| Platycodi Radix (Petroleum ether extract) | 2.4 |
| Leonuri Herba (Petroleum ether extract) | 4.9 |
| Dioscoreae Rhizoma (Petroleum ether extract) | 7.1 |

As shown in Table 1, ceramide production-accelerating effect on human keratinocytes by the plant extract of the present invention was confirmed.

What is claimed is:

1. A method for accelerating ceramide production in a normal human keratinocyte comprising
    administering an extract of a plant selected from the group consisting of *Angelicae Dahuricae Radix, Atractylodis Rhizoma, Bletilla Tuber, Polygoni Multiflori Radix, Platycodi Radix, Leonuri herba,* and *Dioscoreae Rhizoma,* as an active ingredient to the normal human keratinocyte,
    wherein the extract is a petroleum ether extract prepared by using petroleum ether as an extraction solvent, and
    wherein, as a result of the administering, ceramide production in the keratinocyte is accelerated.

2. The method according to claim 1, wherein the plant is *Leonuri herba*.

3. A method of moisturizing skin, comprising
    administering an extract of the plant *Leonuri herba,* as an active ingredient to the skin,
    wherein the extract is a petroleum ether extract prepared by using petroleum ether as an extraction solvent, and
    wherein, as a result of the administering, the skin is moisturized.

4. The method according to claim 1, wherein 0.001 to 1000 mg per day of the extract is administered.

5. The method according to claim 3, wherein 0.001 to 1000 mg per day of the extract is administered.

6. A method for accelerating ceramide production in a normal human keratinocyte, said method comprising
    administering, to the keratinocyte, 0.001 to 1000 mg per day of a *Leonuri herba* extract,
    wherein said extract is administered as an external preparation for skin that comprises 0.001% to 10% by mass of said extract (dry solid content) as an active ingredient, and
    wherein said extract is a petroleum ether extract prepared by using petroleum ether as an extraction solvent, and
    wherein, as a result of the administering, ceramide production in the keratinocyte is accelerated.

7. A method for moisturizing skin, said method comprising
    administering, to the skin, 0.001 to 1000 mg per day of a *Leonuri herba* extract,
    wherein said extract is administered as an external preparation for skin that comprises 0.001% to 10% by mass (dry solid content) of said extract as an active ingredient, and
    wherein said extract is a petroleum ether extract prepared by using petroleum ether as an extraction solvent, and
    wherein, as a result of the administering, the skin is moisturized.

8. The method of claim 1, wherein the extract is administered as an external preparation for skin.

9. The method of claim 3, wherein the extract is administered as an external preparation for skin.

* * * * *